(12) United States Patent
Zehr et al.

(10) Patent No.: US 6,412,342 B1
(45) Date of Patent: Jul. 2, 2002

(54) DEVICE FOR MEASURING PROPERTIES OF A TEXTILE PRODUCT

(75) Inventors: Jürg Zehr; Diego Madone; Walter Isotton, all of Uster (CH)

(73) Assignee: Zellweger Luwa AG (CH)

( * ) Notice: Subject to any disclaimer, the term of this patent is extended or adjusted under 35 U.S.C. 154(b) by 0 days.

(21) Appl. No.: 09/267,380

(22) Filed: Mar. 15, 1999

(30) Foreign Application Priority Data

Mar. 13, 1998 (CH) .............................................. 0613/98

(51) Int. Cl.$^7$ ................................................ G01L 05/04
(52) U.S. Cl. ........................................ 73/160; 73/159
(58) Field of Search .................................. 73/160, 159

(56) References Cited

U.S. PATENT DOCUMENTS

| | | | | |
|---|---|---|---|---|
| 2,950,436 A | * | 8/1960 | Butticaz | 73/160 |
| 3,788,138 A | * | 1/1974 | Heusser | 73/160 |
| 4,706,014 A | * | 11/1987 | Fabbri | 73/160 |
| 4,845,983 A | * | 7/1989 | Heusser | 73/160 |

FOREIGN PATENT DOCUMENTS

| | | |
|---|---|---|
| DE | 24 37 738 | 2/1976 |
| DE | 28 31 242 | 1/1980 |
| DE | 40 25 899 | 2/1992 |
| EP | 0 266 614 | 5/1988 |
| EP | 0 578 975 | 1/1994 |

\* cited by examiner

*Primary Examiner*—Hezron Williams
*Assistant Examiner*—Katina Wilson
(74) *Attorney, Agent, or Firm*—Burns, Doane, Swecker & Mathis, L.L.P.

(57) ABSTRACT

The invention relates to a device for measuring properties of a textile test specimen in a measuring gap (2), in which the textile test specimen is introduced, the measuring gap being formed by two walls. In order to provide a device of the type described, with which adjustment of the guide is simplified and with which the test specimen is nevertheless guided with sufficient accuracy, there is provided in the measuring gap a guide element (15) for the test specimen, which is associated with a wall and adjusted in a stationary manner relative to said wall.

10 Claims, 3 Drawing Sheets

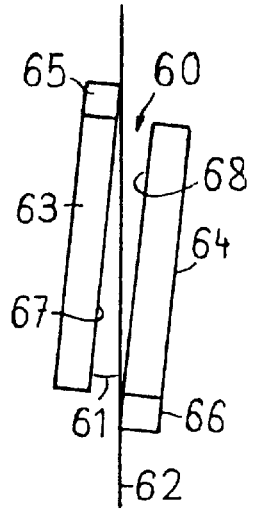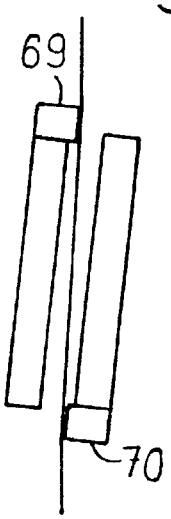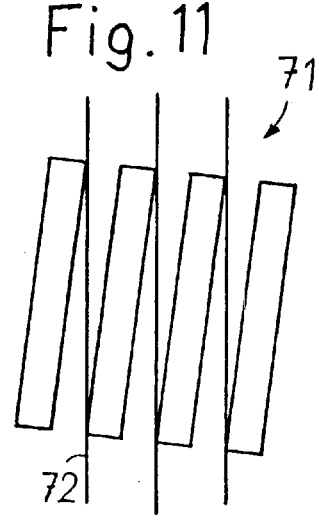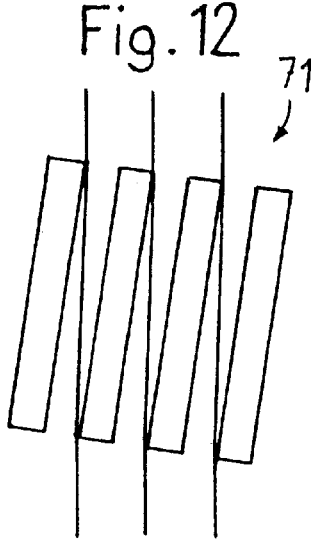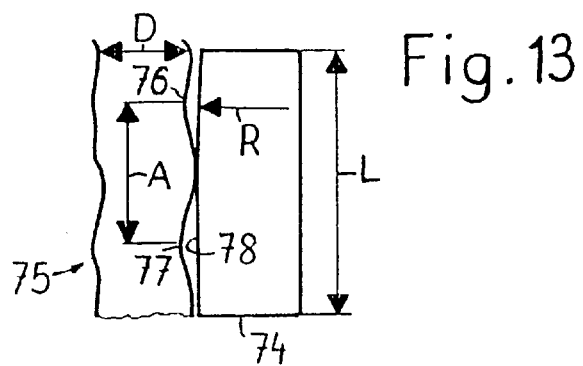

DEVICE FOR MEASURING PROPERTIES OF A TEXTILE PRODUCT

The invention relates to a device for measuring properties of a textile test specimen in a measuring gap, in which the textile test specimen is introduced, the measuring gap being formed by two walls.

Such a device is known, e.g. from EP 0 266 614. The entire disclosure of its counterpart U.S. Pat. No. 4,845,983 is incorporated herein by reference. In such devices, a measuring comb provides a plurality of measuring gaps of differing width, through which the test specimen is guided. The guiding of the test specimen in the measuring gaps is in this case effected by a thread guiding device and a forward feed device, both of which are disposed in separate and exchangeable modules, which are separable from the module with the measuring comb. The thread guiding device and the forward feed device together tension the test specimen so that it runs rectilinearly between said elements and hence also in the measuring gap. Both the thread guiding device and the forward feed device are disposed at a specific distance from the measuring gap.

A perceived drawback of the described device is that the guiding device has to be adjusted precisely in such a way that the test specimen is situated as precisely as possible in a predetermined location, e.g. in the middle of the measuring gap, when it is moved through the latter. Such adjustment of the guiding device has to be effected with great care and accuracy because, e.g. in devices intended for testing yarn, the width of a measuring gap is 1 mm or less. In addition, it is difficult with the human eye to see the conditions in the measuring gap and identify the distances there. The position of the guide or of the measuring gap has to be readjusted after each removal or installation of the module with the guide or with the measuring comb.

An object of the present invention is to provide a device of the type described, with which adjustment of the guide is simplified and with which the test specimen is nevertheless guided with sufficient accuracy.

This is achieved according to the invention by providing in the measuring gap a guide element for the test specimen, which is associated with the wall and adjusted in a stationary manner relative to said wall. The guide element is preferably firmly connected to the wall or is even part of said wall. In said case, the guide element may be placed onto the wall or inserted into the wall. It may project beyond the wall or be aligned with, i.e. not project beyond, the wall. The guide element may be disposed in such a way that it deflects the test specimen from its original path or from its direction of motion, or the measuring gap with the guide element may be aligned in such a way that the test specimen is practically not deflected.

The advantages achieved by the invention are in particular that there is no need for measures to achieve subsequent mutual alignment of the guide element and the measuring gap. The adjustment is effected once for a very long period, e.g. until the guide element presents a degree of wear by the test specimen which is significant in relation to the width of the measuring gap. The type of guidance according to the invention is suitable both for individual measuring gaps and for a plurality of adjacent measuring gaps, which together form a so-called measuring comb. The guides may be designed in such a manner that they offer as little resistance as possible to the movement of the test specimen.

There follows a detailed description of the invention by way of examples and with reference to the accompanying drawings. The drawings show in:

FIG. 1 a device according to the invention having a plurality of measuring gaps, FIGS. 2 to 4 as well as 9 and 10, in each case, a simplified view of a measuring gap, FIGS. 5 and 6 as well as 11 and 12, in each case, a simplified view of a plurality of adjacent measuring gaps, FIGS. 7 and 8, in each case, part of a measuring gap and FIG. 13 part of the measuring gap.

FIG. 1 shows a part 1 of a device for measuring properties of a textile test specimen, having a plurality of measuring gaps 2, 3, 4 and 5 which together form a measuring comb 6. The measuring gaps 2 to 5 lie between plate-like elements 7, 8, 9, 10 and 11 which are used, for example, as carriers for electrodes of capacitors or measuring cells, which are not visible here. The measuring gaps 2 to 5 are each delimited on both sides by walls, which are hardly visible here and are therefore not described in detail. Said walls however correspond to the wall 12 of the element 7, which is visible here, and additionally carry, for example, electrodes as measuring elements in the manner described, for example, in Swiss patent application No. 2926/97 and the entire disclosure of its counterpart U.S. Pat. 6,072,319 is incorporated herein by reference. The measuring comb 6 in the present case is fastened on a support plate 13, which in turn is disposed in a housing 14. The part 1 shown here is, for example, part of a yarn testing apparatus of the type which is known for testing properties of yarns.

Associated with each element 7, 8, 9, 10, and hence also with the walls of said elements, is one of the guide elements 15, 16, 17 and 18 which are shown here. Said guide elements 15 to 18 are each fastened on, or at least disposed in a stationary manner relative to, one of the elements 7 to 10 so that they too occupy a fixed position relative to a wall. Between the walls or elements 7 to 11 a test specimen, e.g. a yarn, sliver, filament etc., is to be moved in its longitudinal direction in a manner which is known per se and therefore not shown in detail here, in FIG. 1, for example, from top to bottom. During said process, the test specimen moves along one of the guide elements 15 to 18. Although they are not visible here, guide elements are likewise disposed also at the bottom end of the measuring gaps 2 to 5. The guide elements 15 to 18 may, for example, be configured in such a way that they facilitate insertion of the test specimen. This is effected, for example, by means of lead-in bevels such as are denoted here, for example, on the guide element 16 by 73. The elements 7 to 11 and the guide elements 15 to 18 may be designed and disposed relative to one another in many different ways, as is evident from the Figures described below.

FIG. 2 shows a measuring gap 20 having guide elements 21, 22, which are both associated with the same wall 23 or the same plate-like element 24 and are in particular disposed on the latter and on the wall 23 so as to project beyond said wall. Thus, the test specimen 25 is guided at a defined distance from the one wall 23. Here, both guide elements 21, 22 project by the same amount so that the test specimen 25 lies parallel to the wall 23.

FIG. 3 shows a measuring gap 26 having guide elements 27, 28 which, in relation to the measuring gap 26, viewed in longitudinal direction and transverse direction lie at opposite sides of the measuring gap 26. In the illustrated arrangement, the two guide elements 27 and 28 do not project as far as the middle of the measuring gap 26 so that the test specimen 29 does not necessarily run parallel to the walls 30 and 31 and occupies another position which is advantageous for the measuring process.

FIG. 4 shows a further measuring gap 32, where the guide elements 33, 34 are integrated into the elements 35, 36 and therefore do not project beyond the walls 37, 38. The test specimen 39 in said case does not lie parallel to the walls 37, 38 in the measuring gap 32. Since, for example, the electrodes of a measuring cell in a measuring gap do not take up the entire surface area of the walls 37, 38 and are therefore inserted or attached only in specific regions of said walls, the carrier material, from which the elements 35, 36 are made, may be provided in its entirety or only locally with properties suitable for guiding the test specimen 39.

FIG. 5 shows a measuring comb having a plurality of measuring gaps 40, 41, 42, which are not of the same width and in which the test specimen is guided, in the manner shown in FIG. 2, at the same side or in front of the same wall. Thus, one element 43 has no guide elements.

FIG. 6 shows a measuring comb having a plurality of measuring gaps 44, 45, 46 and 47, with guide elements 48, 49, 50 and 51 being disposed only on two elements 52 and 53. Each guide element is in said case of a double-action design, i.e. it has, on two sides, guide faces for two test specimens.

FIG. 7 shows a part of an element 54, in which the guide element 55 is integrated and has a guide face 56, which projects beyond a wall 57.

FIG. 8 shows a guide element 59, which is inserted into a plate-like element 58 and the latter's wall and fastened therein.

FIG. 9 shows a measuring gap 60, which is inclined at an angle 61 relative to the test specimen 62. Associated with the plate-like elements 63 and 64 are guide elements 65 and 66, which do not project beyond the walls 67 and 68.

FIG. 10 shows a similar construction to that according to FIG. 9 but with projecting guide elements 69 and 70. The latter are arranged alternately each at one end of a platelike element or wall.

FIG. 11 shows a measuring comb 71 having integrated guide elements according to FIG. 4, which is aligned in such a way that the test specimen 72 is not deflected.

FIG. 12 shows the same measuring comb 71 as FIG. 11, which is however further inclined so that the test specimen is slightly deflected.

Naturally, further combinations particularly with groups of plate-like elements and guide elements are conceivable, which constitute a construction in the sense of the claims even though they are not expressly illustrated here.

FIG. 13 shows a special construction of a guide element 74 for a test specimen 75 having, for example, periodic irregularities which are represented here, for example, by bumps or depressions 76, 77 in its surface. An example of this is a twisted yarn made from a plurality of filaments. To prevent vibration of the test specimen moved in its longitudinal direction, the length L of the guide element 74 is to be greater than a distance A between said bumps or depressions. The radius R of a guide face 78 is to be substantially greater than the diameter D of the test specimen. of particular advantage is a radius R, which is at least twenty times said diameter D.

Figure 1:
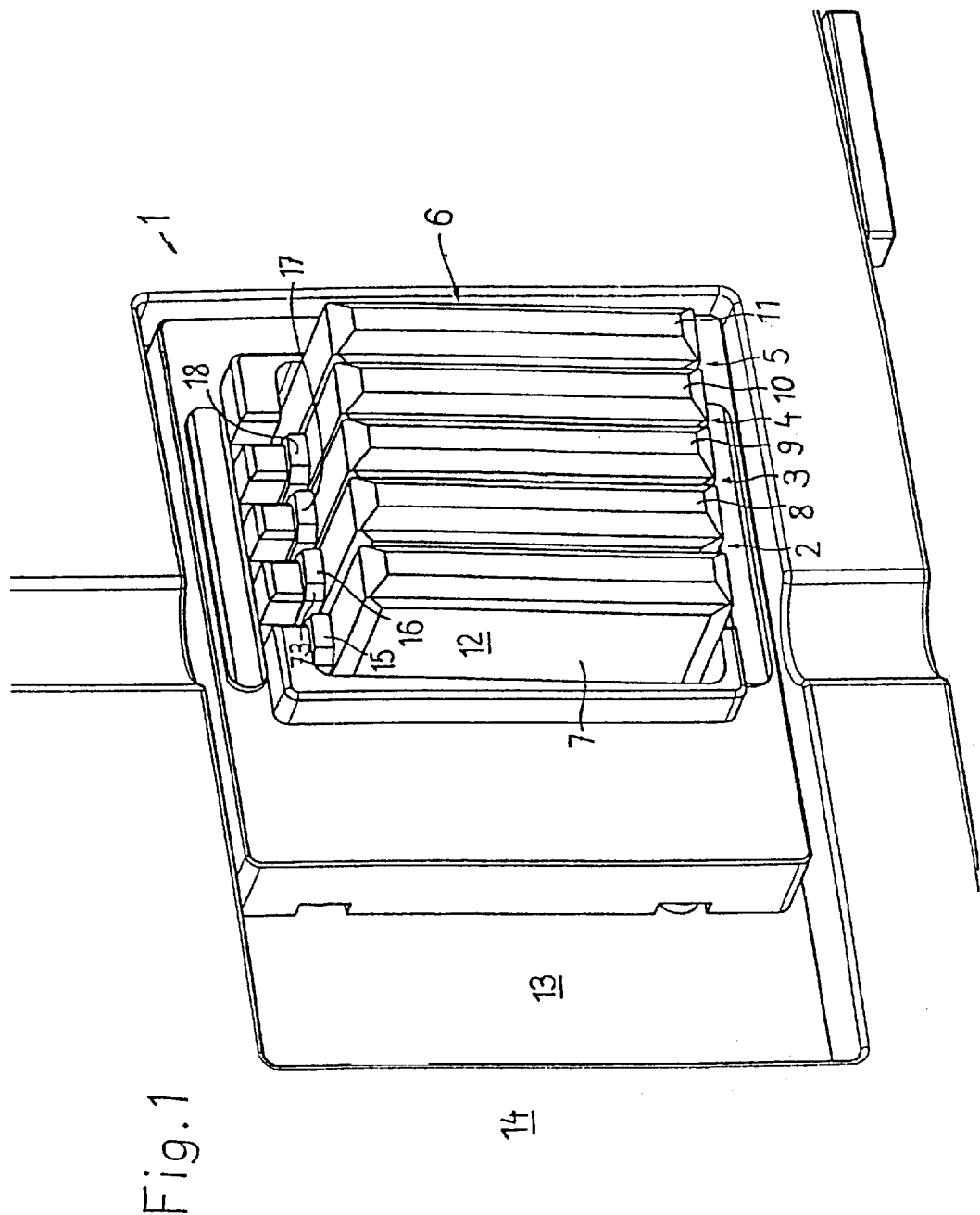
Figure 2:
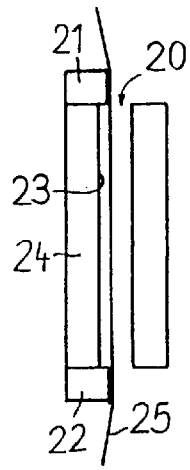
Figure 3:
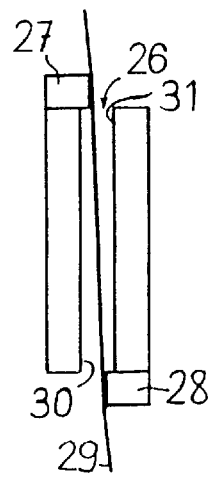
Figure 4:
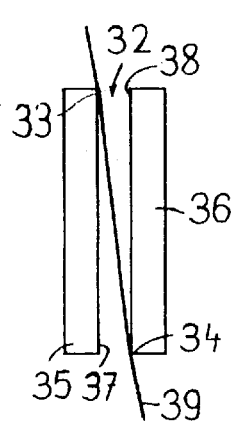
Figure 5:
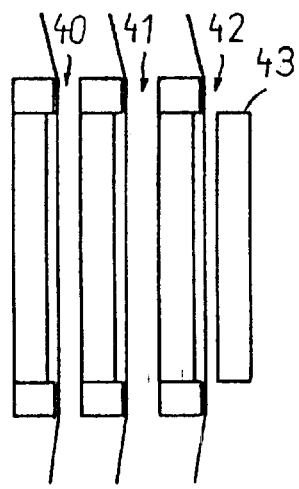
Figure 6:
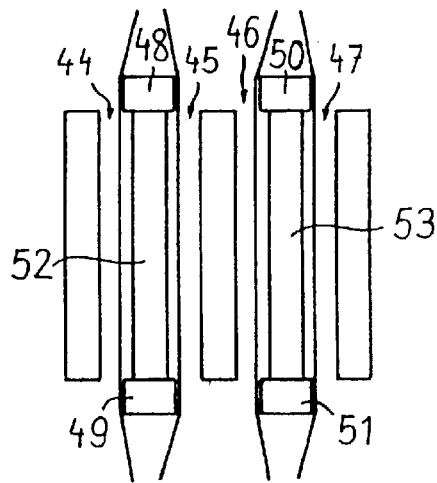
Figure 7:
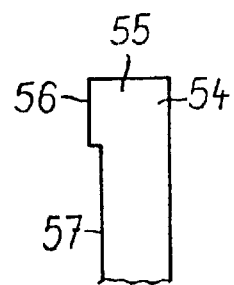
Figure 8:
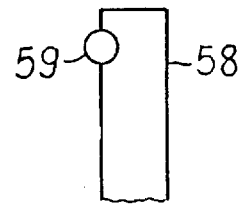

The mode of operation of the device according to the invention is in said case as follows: For measurement of its properties, the test specimen is inserted into one of the measuring gaps 2, 3, 4 or 5 and pushed rearwards until it passes into the region of the guide elements 15 to 18. By means of the drive, the test specimen is moved in its longitudinal direction and hence also tensioned so that it is applied over the guide faces of the guide elements of said measuring gap. By said means the test specimen is accurately positioned in the measuring gap and lies at the correct point in the measuring field of the measuring gap. As is known from FIGS. 2, 5 and 6, the test specimen may in said case lie parallel to the walls of the measuring gap or it may, as shown in FIGS. 3, 4 and 9 to 12, move or lie diagonally through the width of the measuring gap. Said position of the test specimen in the measuring gap is very advantageous because the test specimen always moves through the middle of the measuring gap. This being the case at least when the measuring gap with the guide elements is of a symmetrical construction. Thus, the possibility is also created of designing the measuring comb so as to be capable of swivelling in order for example, in one position, e.g. according to FIG. 1 or 11, to facilitate the introduction of the test specimen from the front and, in another position, to guarantee reliable guidance with suitable deflection of the test specimen.

What is claimed is:

1. In yarn testing apparatus comprising a yarn guiding device, a measuring unit, and feeding means for pulling the yarn lengthwise along a path extending from the yarn guiding device, through said measuring unit and to said feeding means, the improvement which comprises a measuring unit having first and second parallel walls spaced apart from one another to form therebetween a measuring gap through which the yarn moves and wherein said walls are inclined relative to a straight line from said guiding device to said feeding means so that the moving yarn is adjacent to one of the measuring gap walls as it enters the measuring gap and is adjacent to the other measuring gap wall as it exists the measuring gap.

2. Yarn testing apparatus according to claim 1, wherein said measuring unit includes a first guide surface for contacting the yarn as it enters said measuring gap and a second guide surface for contacting the yarn as it exits from said measuring gap.

3. Yarn testing apparatus according to claim 2, wherein said first guide surface deflects the yarn from a straight line extending between said yarn guiding device and said feeding means.

4. Yarn testing apparatus according to claim 3, wherein said second guide surface deflects the yarn from a straight line extending from said first guide surface to said feeding means.

5. In yarn testing apparatus comprising a yarn guiding device, a measuring unit, and feeding means for pulling the yarn lengthwise from said guiding device and through said measuring unit, the improvement which comprises a measuring unit having first and second walls forming therebetween a measuring gap through which said yarn moves, said measuring unit including a first guide surface positioned to contact the yarn adjacent its entry to said measuring gap, and a second yarn guide surface positioned to contact the yarn adjacent its exit from said measuring gap, said second yarn guide surface being so positioned relative to said first yarn guide surface as to cause the yarn to move through said gap along a path that is spaced from both of said walls in a zone between the entrance end of said gap and the exit end of the gap.

6. Yarn testing apparatus according to claim 5, wherein both of said first and second guide surfaces are fixed positionally with respect to one of said walls.

7. Yarn testing apparatus according to claim 5, wherein said first guide surface is fixed positionally with respect to said first wall and said second guide surface is fixed positionally with respect to said second wall.

8. Yarn testing apparatus according to claim 5, wherein at least one of said guide surfaces is integral with one of said walls.

9. Yarn testing apparatus according to claim 5, where at least one of said guide surface is a surface of a member attached to one of said walls.

10. In yarn testing apparatus comprising a yarn guiding device, a measuring unit, and a yarn feeder arranged to draw the yarn lengthwise along a path extending from the yarn guiding device, through said measuring unit and to said feeder, the improvement which comprises a measuring unit having first and second parallel walls spaced apart from one another to form therebetween a measuring gap through which the yarn moves and wherein said walls are inclined relative to a straight line from said guiding device to said feeder, a first guide surface fixed with respect to said first wall at a location to contact said yarn as it enters the measuring gap, and a second guide surface fixed with respect to said second wall at a location to contact said yarn as it exits the measuring gap.

* * * * *